(12) United States Patent
Parker

(10) Patent No.: US 6,383,473 B1
(45) Date of Patent: *May 7, 2002

(54) SOLID COMPOSITION FOR REDUCING TOOTH EROSION

(75) Inventor: David Myatt Parker, Hereford (GB)

(73) Assignee: SmithKline Beecham p.l.c., GBX (*) Notice: Subject to any disclaimer, the term of this patent is extended or adjusted under 35 U.S.C. 154(b) by 0 days.

This patent is subject to a terminal disclaimer.

(21) Appl. No.: 09/485,898
(22) PCT Filed: Aug. 11, 1998
(86) PCT No.: PCT/EP98/05119
§ 371 Date: Feb. 17, 2000
§ 102(e) Date: Feb. 17, 2000
(87) PCT Pub. No.: WO99/08550
PCT Pub. Date: Feb. 25, 1999

(30) Foreign Application Priority Data

Aug. 19, 1997 (GB) .............................. 9717598

(51) Int. Cl.[7] .................. A61K 33/06; A61K 7/16; A61K 7/24; A23L 2/52; A23L 2/60
(52) U.S. Cl. .................. 424/55; 426/74; 426/590; 426/648; 426/650; 426/682
(58) Field of Search .................. 424/49.58, 55; 426/74, 590, 648, 650, 682

(56) References Cited

U.S. PATENT DOCUMENTS

| | | | |
|---|---|---|---|
| 5,028,446 A | 7/1991 | Saleeb et al. | 426/590 |
| 5,424,082 A | 6/1995 | Dake et al. | 426/72 |
| 5,445,837 A | 8/1995 | Burkes et al. | 426/74 |
| 5,468,506 A | 11/1995 | Andon | 426/74 |
| 5,474,793 A | 12/1995 | Meyer et al. | 426/599 |
| 5,500,232 A | 3/1996 | Keating | 426/74 |
| 5,597,595 A | 1/1997 | DeWille et al. | 426/74 |
| 5,690,975 A | 11/1997 | Akahoshi et al. | 426/34 |
| 5,817,351 A | 10/1998 | DeWille et al. | 426/74 |

FOREIGN PATENT DOCUMENTS

| | | |
|---|---|---|
| EP | 0 117 653 | 1/1984 |
| EP | 0227174 | 7/1987 |
| EP | 0 244 903 | 11/1987 |
| EP | 0 301 653 | 2/1989 |
| EP | 0 587 972 | 3/1994 |
| EP | 0 634 110 | 7/1994 |
| EP | 0 713 652 | 5/1996 |
| GB | 1 250 535 | 10/1971 |
| GB | 1 516 525 | 7/1978 |
| GB | 2 207 335 | 2/1989 |
| WO | WO 8803762 | 6/1988 |
| WO | WO88/03762 | 6/1988 |
| WO | WO92/05711 | 4/1992 |
| WO | WO97/21356 | 6/1997 |
| WO | WO 9730601 | 8/1997 |
| WO | WO 9813012 | 4/1998 |
| WO | WO 9813013 | 4/1998 |

OTHER PUBLICATIONS

Lussi et al., (I), *Caries Research* 27(5):pp. 387–393 (1993) "The Influence of Different Factors On In Vitro Enamel Erosion".

Lussi et al., (II), *Caries Research* 29(5):pp. 349–354 (1995) "Prediction of the Erosive Potential of Some Beverages".

*Primary Examiner*—Zohreh Fay
*Assistant Examiner*—Brian-Yong Kwon
(74) *Attorney, Agent, or Firm*—Dara L. Dinner; Stephen Ventianer; Charles M. Kinzig

(57) ABSTRACT

Acidic oral compositions having reduced tooth erosion characteristics, especially acid beverages such as fruit juice drink concentrates, or oral healthcare products such as mouthwashes, are prepared by adding a calcium compound to the acid composition so that the mol ratio of calcium to acid ranges from 0.3 to 0.8, and the pH of the composition, if necessary after adjustment with an alkali, is from 3.5 to 4.5.

8 Claims, No Drawings

SOLID COMPOSITION FOR REDUCING TOOTH EROSION

This application is a 371 of PCT/AT99/00284, filed on Aug. 11, 1998.

The present invention relates to compositions for oral use, in particular solid or semi-solid acidic products and oral healthcare compositions, and to the use of calcium in such compositions to alleviate or prevent the tooth damage associated with the consumption of acid. In particular, the present invention alleviates palatability problems associated with calcium addition to products.

It is thought that erosion of teeth is caused inter alia by acidic foodstuffs leaching out calcium from the teeth faster than it can be replaced by normal remineralisation processes. When a product is prepared in accordance with this invention, and introduced into the oral cavity for consumption or healthcare purposes, the dissolution or removal of calcium and phosphate from teeth by chemical processes is significantly reduced.

Calcium is the most abundant mineral in the body. The vast majority of calcium is deposited in the bones and teeth but the mineral is also essential for other bodily functions such as the regulation of nerve function. the contraction of muscles and clotting of blood. Calcium is a common constituent of beverages being derived from fruit ingredients and from hard water when this is used in beverage production without prior softening. Values for the concentration of calcium occurring in this way are typically in the range 0.005–0.02% w/w. Interest in the general nutritional benefits of diet fortification by calcium ion has led to a search for practical ways to incorporate this ion at higher levels from 0.02% w/w to 2% w/w. The use of calcium as a supplement for beverages has been described in WO88/03762.

It is well known that the addition of malic acid will help maintain the solubility of calcium in calcium fortified beverages therefore minimizing losses due to precipitation. This is because of the formation of a soluble complex "calcium citrate malate". On the other hand, Lussi et al (1995, Caries Res 29, 349–354) have associated the titratable acidity of a beverage with its erosive potential; the greater the concentration of acid in the beverage the more damaging to teeth it became.

In EP 551398 (Procter & Gamble) there is disclosed a method for preventing the erosion of tooth enamel by consuming an acid beverage (having a pH of lees than 5.5) comprising from 0.02% to 0.15% of calcium in the form of a calcium citrate malate complex having a molar ratio of citrate to malate of 1:0.5 to 1:4.5. In the calcium citrate malate complexes the molar ratio of total moles calcium:total moles citrate:total moles malate may be from about 2:1:1 to about 6:3:4. A preferred complex for beverages has the molar ratio 4:2:3. U.S. Pat. No. 5,073,389 describes the use of calcium citrate malate to provide a mineral supplemented candy product.

We have found that inclusion of high levels of calcium in products gives palatability problems. However, we have found that effective reduction of tooth erosion in acidic oral compositions can be achieved without impairing palatability using lower amounts of calcium relative to the acidulant when the pH of the composition is also controlled. WO 97/30601 (published Aug. 28, 1997) discloses controlled pH liquid compositions containing calcium and an acidulant in a defined ratio.

The present invention provides a solid or semi solid composition for oral use containing a calcium compound and an acidulant characterised in that calcium is present in the range of 0.3 to 0.8 mol per mol of acid and that the amount of calcium and acidulant in the composition is selected so that the effective pH of the composition is from 3.5 to 4.5.

The term effective pH is used in the context of the present invention to mean the pH of the composition before solidification (where the composition is prepared via a liquid phase intermediate) or the pH of the composition when reconstituted or dissolved in a liquid, eg. water. The term solidification encompasses the treatment or supplementation of liquid phase intermediates to form a solid or semi-solid.

In another aspect, the present invention provides the use of calcium as a tooth erosion inhibitor in a solid or semi-solid acidic composition for oral administration comprising a calcium compound and an acidulant, characterised in that calcium is present in the range of 0.3 to 0.8 mol per mol of acid and that the amount of calcium and acidulant in the composition is selected so that the effective pH of the composition is from 3.5 to 4.5.

In a further aspect, the present invention provides a method of reducing the tooth erosion potential of a solid or semi-solid acidic oral composition comprising adding calcium to the acidic oral composition so that calcium is present in the range of 0.3 to 0.8 mol per mol of acid and the effective pH is from 3.5 to 4.5, obtaining an effective pH within the range 3.5 to 4.5 by addition of an alkali, if necessary or desired.

The invention also extends to a method of reducing tooth erosion caused by acid in orally administered compositions comprising orally administering a solid or semi-solid composition comprising a calcium compound and an acidulant, characterised in that calcium is present in the range of 0.3 to 0.8 mol per mol of acid and that the amount of calcium and acidulant in the composition is selected so that the effective pH of the composition is from 3.5 to 4.5.

The invention further extends to the use of a solid or semi-solid composition comprising a calcium compound and an acidulant in the manufacture of a medicament for the reduction of tooth erosion caused by acid in orally administered compositions, characterised in that calcium is present in the range of 0.3 to 0.8 mol per mol of acid and that the amount of calcium and acidulant in the composition is selected so that the effective pH of the composition is from 3.5 to 4.5.

In a still further aspect, the present invention provides a process for preparing a composition of this invention which comprises mixing a calcium compound with an acidulant so that calcium is present in the range of 0.3 to 0.8 mol per mol of acid and the effective pH of the composition is from 3.5 to 4.5. If necessary or desired an effective pH within the range 3.5 to 4.5 can be obtained by addition of an alkali.

The present invention is particularly applicable to solid or semi solid acidic substances for oral consumption such as boiled sweets, candies, tablets, lozenges, lollies, chews, jellies, gums, drops, dry powder blends such as powdered drinks intended for dissolution, eg. in water, and the like. Semi solid products also include dairy products such as yoghurts and set or frozen drinks.

Suitably the composition before solidification is prepared and tested using the techniques described in WO 97/30601, the entire contents of which are herein incorporated by reference.

The effective pH for compositions of the invention is higher than normally associated with acid-based products for human consumption which typically have an effective pH of about pH 3 in order to maintain palatability associated with sharpness in taste. Practice of the present invention does not cause taste defects in products. Although an increase in effective pH to around pH 4 would be expected to reduce the sharpness in taste provided by the acidulant, surprisingly the inclusion of calcium in accordance with this invention mitigates this.

A further advantage arises from the use of low levels of calcium in accordance with this invention, suitably in the form of an alkaline salt. The buffering capacity of the formulation is reduced by partial neutalisation of the acid, which allows saliva to neutralise remaining acid residues in the mouth more rapidly.

The absolute concentration of calcium used in the compositions of the present invention is not critical as this will vary according to the nature and concentration of the acids present. The acid composition may contain organic and/or inorganic acids and may be supplemented with vitamins such as ascorbic acid. The calcium concentration may vary from 0.001 mol. per liter to more than 0.25 mol. per liter, typically from 0.002 mol. per liter to 0.1 mol. per liter, suitably from 0.01 mol. per liter to 0.05 mol.per liter.

The calcium may be added in any suitable form, conveniently as a soluble salt such as calcium carbonate, calcium hydroxide, calcium citrate, calcium malate, calcium lactate, calcium chloride, calcium glycerophosphate or calcium formate or any other salt which minimises any adverse flavour contribution to the composition.

Compositions of the invention may be prepared by mixing the acid (e.g. citric acid) with its corresponding calcium salt (e.g. calcium citrate) or another calcium salt. It may be advantageous to mix the acid with an alkaline calcium salt such as calcium carbonate or calcium hydroxide thereby minimizing the concentration of acid applied to the formulation. The acid can also be mixed with inorganic calcium salts such as calcium chloride. The molar ratio of calcium to acid may be 0.3 to 0.75, typically 0.3 to 0.7, more typically 0.3 to 0.65, suitably 0.3 to 0.60 and preferably 0.3–0.55 or 0.4 to 0.55. Most preferably the molar ratio is at least 0.4, and a value of about 0.5 has been found to be especially effective.

The effective pH of the formulation may be adjusted to the desired range by the addition of the calcium compound to the appropriate proportion relative to the acid. If necessary, depending on the acid present, the effective pH may be further adjusted by the application of an alkali e.g. sodium hydroxide or a suitable salt for example sodium citrate, sodium malate or sodium lactate. The effective pH of the composition is preferably not more than 4, most preferably from 3.7 to 3.9. Compositions with an effective pH of about 3.8 have been found to be especially effective.

Typically the acid concentration in compositions of the invention, for example the citric acid or malic acid concentration in a fruit-based product would be in the range 0.01% w/w to 4% w/w, suitably in the range 0.1% w/w to 1% w/w. Other potable acids conventional for products of the invention may also be used, such as lactic acid. Mixtures of potable acids may be used.

In a preferred embodiment, the acid composition is based on a concentrate prepared from a natural fruit juice, such as blackcurrant juice, for example a flavoured syrup concentrate. The calcium may be added in a suitable form to the concentrate and the resulting composition is formed into a solid or semi-solid. Preferably the product contains reduced levels of sugar or carbohydrate or is of low calorie type containing intense sweeteners.

The oral composition may contain magnesium or other ions as adjuncts for remineralisation. It may also contain an effective amount of malic acid or potable salts thereof to maintain the solubility of the calcium so as to prevent or minimize the precipitation of insoluble calcium salts. Added malic acid may provide as little as 10% of the total acidity of the beverage, the remainder of the acidity being provided by other, preferably naturally present, acids such as citric acid, or by ascorbic acid.

The invention may be applied in a variety of products based on concentrates, in particular to health products containing blackcurrant juice or extract or added vitamins. The compositions are typically solidified according to known methods such as freezing, cooking, gelling or by the formation of solid or semi solid emulsions or gels. Suitable formulation techniques can be found in standard confectionary texts such as 'Sugar Confectionary Manufacture' by E. B. Jackson (2nd Edition).

The invention is advantageously applied to products containing natural or added citric acid. The products may be unsweetened or sweetened with sugar or intense sweeteners such as saccharine, aspartyl phenyl alanyl methyl ester, or other sweeteners known in the art. The products may also contain other conventional additives such as sodium benzoate, sorbic acid, sodium metabisulfite, ascorbic acid, flavourings and colourings.

The products may be prepared by mixing the ingredients according to conventional methods. Ingredients may be dissolved in water or in hot water, if required, prior to addition to the other components. Typically concentrates are pasteurised.

The invention is illustrated by the following Examples:

EXAMPLE 1

A concentrated product is initially prepared by mixing the ingredients as follows. The calcium carbonate is added to the other ingredients as a final addition.

| | |
|---|---:|
| Blackcurrant juice concentrate SG 1.27 | 84 liter |
| Aspartyl phenyl alanyl methyl ester* | 1.15 Kg |
| Acesulfame K | 1.8 Kg |
| Ascorbic acid | 0.8 Kg |
| Sodium benzoate | 0.325 Kg |
| Sodium metabisulfite | 0.145 Kg |
| Blackcurrant flavouring | 0.3 liter |
| Water | up to final volume 1000 liter |
| Calcium carbonate | 4.2 Kg |

*sold as Aspartame (RTM)

The mol ratio of calcium : acid is 0.5

The concentrate is adjusted to pH 3.7 with sodium hydroxide solution. In-vitro planometry tests can be performed on the concentrate formulations as follows. Flat dental enamel sections are exposed to test solutions having a pH of 3.85 (×5 dilution of concentrate with water) at a temperature of 37° C. for 30 minutes. Erosive potential is evaluated by physical measurement of the depth of enamel lost during the procedure. Whereas a control formulation comprising 14 mM citric acid, pH 3.2 results in a loss of 4 microns of enamel and a further control formulation of 14 mM citric acid, pH 3.85, removes 1.8 microns, a test formulation with adjusted pH and added calcium comprising 14 mM citric acid, 7 mM calcium, pH 3.85 removes only 0.17 microns of enamel, demonstrating the utility of the invention.

This solution or the concentrate before dilution can be solidified according to Example 5 or 6 below.

EXAMPLE 2

A solution was prepared by mixing ingredients as follows:

| Ingredients | % w/v |
|---|---|
| Sodium benzoate | 0.01 |
| Malic acid | 0.30 |
| Flavouring | 0.1 |
| Artificial sweetener | 0.05 |
| Water by difference | 99.5 |
| Calcium hydroxide | 0.083 |

The resultant pH of the composition is typically 3.85 and has a calcium to acid molar ratio of 0.5. This solution can be solidified according to Example 5 or 6 below.

In vitro planometry tests were performed on the solution in which flat dental enamel sections were exposed to test solutions at a temperature of 37° C. for 30 minutes. Erosive potential was evaluated by physical measurement of the depth of enamel lost during the procedure. Whereas a control formulation lacking the addition of calcium hydroxide gave a pH of 2.5 and resulted in a loss of 8.1 microns of enamel and a further control formulation in which the pH had been increased to pH 3.85 with sodium hydroxide removed 1.65 microns, the composition detailed above removed only 0.6 microns of enamel, demonstrating its utility in reducing tooth erosion.

EXAMPLE 3

A solution was prepared by mixing ingredients as follows:

| Ingredients | % w/w |
|---|---|
| Sugar | 10 |
| Sodium benzoate | 0.01 |
| Orange juice | 5.04 |
| Ascorbic acid | 0.03 |
| Citric acid monohydrate | 0.15 |
| Flavouring | 0.005 |
| Colouring | 0.004 |
| Water by difference | 86 |
| Calcium carbonate | 0.048 |
| Sodium hydroxide | sufficient to adjust to pH 3.9 |
| Carbon dioxide | 0.48 |

In this solution the mol ratio of calcium:acid is 0.46 (orange juice is typically 1% w/w citric acid).

This solution is then solidified as further indicated in Example 5 or 6 below.

EXAMPLE 4

A solution was prepared by mixing ingredients as follows:

| Ingredients | % w/w |
|---|---|
| Sugar | 8 |
| Sodium benzoate | 0.01 |
| Apple juice | 10 |
| Ascorbic acid | 0.03 |
| Malic acid | 0.15 |
| Flavouring | 0.005 |
| Colouring | 0.004 |
| Water by difference | 82 |

-continued

| Ingredients | % w/w |
|---|---|
| Calcium carbonate | 0.093 |
| Sodium hydroxide | sufficient to adjust to pH 3.9. |

In this solution the mol ratio of calcium:acid is 0.74 (apple juice is typically 0.6% w/w malic acid). The solution is then solidified as indicated in the Example 5 or 6 below.

EXAMPLE 5

Solidification Techniques

Concentrates can be solidified by freezing e.g. at temperatures less than minus 5 degrees C., preferably at temperatures around minus 20 degrees C. Solutions can be boiled, e.g. for 10 minutes until a set point is reached, followed by cooling and moulding if desired. Dissolved powder gelatine can be added (according to manufacturer's instructions) and the product allowed to set.

EXAMPLE 6

| Blackcurrant jellies | |
|---|---|
| Ingredients | grammes |
| Glucose syrup | 564 |
| Gelatin 190 bloom | 93 |
| Water | 152 |
| Concentrate (e.g. Example 1) | 191 |

The glucose syrup is cooked to 85% solids and the gelatine soaked in warm water to dissolve. The gelatine solution and concentrate is added to the glucose syrup solution. The mixture is moulded in cornflour and left overnight.

EXAMPLE 7

Dry Powdered Orange Sports Drink

The ingredients are dry blended typically using a ribbon blender until a homogeneous mixture is obtained. The product is then filled into appropriate packaging, such as sachets, jars or drums.

| Ingredients | kg |
|---|---|
| Dextrose Monohydrate | 389.12 |
| Maltodextrin | 523.37 |
| Aspartame | 0.58 |
| Acesulfame k | 0.37 |
| Tri-sodium citrate | 16.54 |
| Sodium chloride | 9.34 |
| Citric acid | 36.97 |
| Ascorbic acid | 1.17 |
| Potassium citrate | 2.33 |
| Calcium carbonate | 11.46 |
| Orange flavour | 2.92 |
| Beta-Carotene (1%) | 5.84 |
| Total | 1000.00 kg |

50 g of the powder was dissolved in 500 ml of water to make an orange sports drink. The drink had a pH of 4 and a calcium to acid molar ratio of 0.6.

EXAMPLE 8

Dry Powdered Low-Calorie Orange Sports Drink

The ingredients are dry blended typically using a ribbon blender until a homogeneous mixture is obtained. The product is then filled into appropriate packaging such as sachets, jars or drums.

| Ingredients | kg |
|---|---|
| Maltodextrin | 129.52 |
| Aspartame | 30.73 |
| Acesulfame k | 9.77 |
| Tri-sodium citrate | 153.07 |
| Sodium chloride | 59.81 |
| Citric acid | 353.23 |
| Ascorbic acid | 27.55 |
| Potassium citrate | 21.55 |
| Calcium carbonate | 109.50 |
| Orange flavour | 35.09 |
| Beta-Carotene (1%) | 70.18 |
| Total | 1000.00 kg |

4 g of the powder was dissolved in 500 ml of water to make a low-calorie orange sports drink. The drink had a pH of 4 and a calcium to acid molar ratio of 0.6.

What is claimed is:

1. A method of reducing tooth erosion caused by acid in orally administered compositions comprising orally administering a solid or semi-solid composition comprising a calcium compound and an acidulant, wherein calcium is present in the range of 0.3 to 0.8 mol per mol of acid and the amount of calcium and acidulant in the composition is selected so that the effective pH of the composition is from 3.5 to 4.5.

2. A method as claimed in claim 1 in which the calcium is present in the range 0.3–0.75 mol per mol of acid.

3. A method as claimed in claim 2 in which the calcium is present in the range 0.3–0.65 mol per mol of acid.

4. A method as claimed in claim 3 in which the calcium is present in the range 0.3–0.60 mol per mol of acid.

5. A method as claimed in claim 4 in which the calcium is present in the range 0.3–0.55 mol per mol of acid.

6. A method as claimed in claim 1 in which the calcium is present in an amount of at least 0.4 mol per mol of acid.

7. A method as claimed in claim 1 which the effective pH of the composition is not more than 4.

8. A method as claimed in claim 7 in which the effective pH is from 3.7 to 3.9.

* * * * *